US00PP25037P2

(12) United States Plant Patent
Reese

(10) Patent No.: US PP25,037 P2
(45) Date of Patent: Nov. 4, 2014

(54) ***KOELERIA* PLANT NAMED 'CORNISH BLUE'**

(50) Latin Name: *Koeleria glauca*
Varietal Denomination: Cornish Blue

(71) Applicant: Nick Reese, Maplehurst (GB)

(72) Inventor: Nick Reese, Maplehurst (GB)

( * ) Notice: Subject to any disclaimer, the term of this patent is extended or adjusted under 35 U.S.C. 154(b) by 109 days.

(21) Appl. No.: 13/815,375

(22) Filed: Feb. 26, 2013

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Susan McCormick Ewoldt
(74) *Attorney, Agent, or Firm* — Penny J. Aguirre

(57) ABSTRACT

A new cultivar of *Koeleria glauca*, 'Cornish Blue', that is characterized by its foliage that is variegated with thin green centers and wide creamy white margins.

2 Drawing Sheets

Botanical classification: *Koeleria glauca.*
Varietal denomination: 'Cornish Blue'.

BACKGROUND OF THE INVENTION

The present invention relates to a new and distinct cultivar of *Koeleria glauca* and will be referred to hereafter by its cultivar name, 'Cornish Blue'. 'Cornish Blue' is a new cultivar of perennial ornamental grass grown for container and landscape use.

The new cultivar was bred and selected by the Inventor in West Sussex, United Kingdom. The Inventor made a cross in September of 2006 between unnamed plants of *Koeleria glauca* as both the female and male parents. The Inventor selected 'Cornish Blue' as a single unique plant amongst the seedlings that resulted from the above cross.

Asexual propagation of the new cultivar was first accomplished by division in West Sussex, United Kingdom in October of 2008 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Cornish Blue' as a unique cultivar of *Koeleria.*

1. 'Cornish Blue' exhibits foliage that is variegated with thin green centers and wide creamy white margins.

The parent plants, unnamed plants of *Koeleria glauca*, differ from 'Cornish Blue' in having non-variegated foliage that is green in color. There are no other cultivars of *Koeleria glauca* with variegated foliage that are known to the Inventor. The only cutivar of *Koeleria glauca* known to the Inventor is 'Blue Sprite', a non-patented seed strain with a dwarf plant habit and blue-green foliage.

BRIEF DESCRIPTION OF THE DRAWING

The accompanying colored photographs illustrate the overall appearance and distinct characteristics of a one year-old plant of the new cultivar as grown outdoors in a 9-cm container in West Sussex, United Kingdom.

The photograph in FIG. 1 illustrates the overall plant habit and appearance of 'Cornish Blue'.

Figure 1:
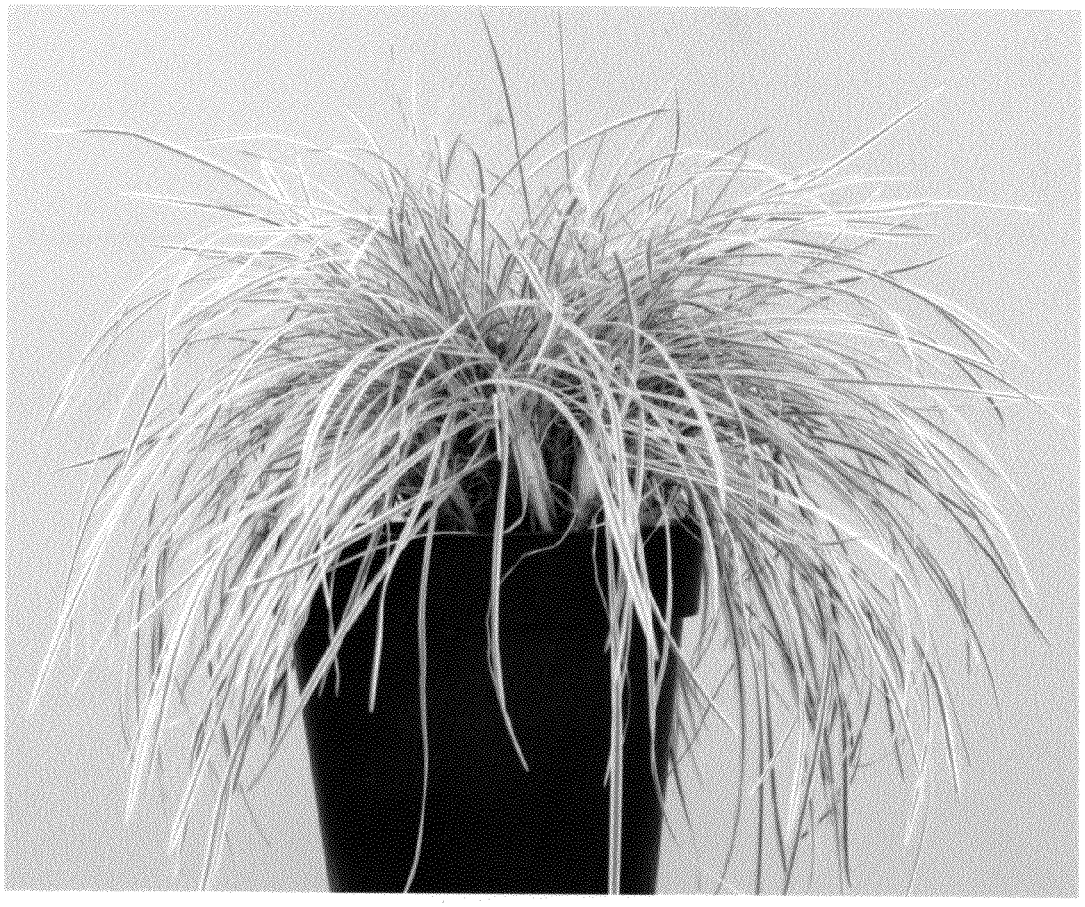
Figure 2:
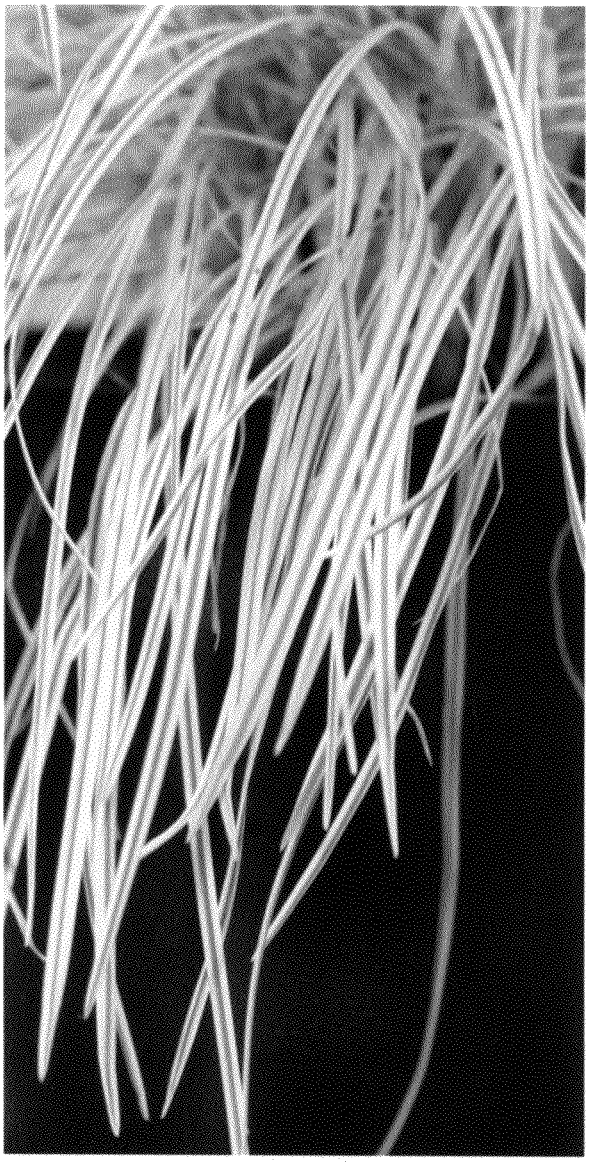

The photograph in FIG. 2 provides a close-up view of the foliage of 'Cornish Blue'. The colors in the photograph may differ slightly from the color, values cited in the detailed botanical description, which accurately describe the colors of the new *Koeleria.*

DETAILED BOTANICAL DESCRIPTION

The following is a detailed description of one year-old plants of the new cultivar as grown outdoors in a 9-cm containers in West Sussex, United Kingdom. The phenotype may vary somewhat with variations in temperature, day-length, light intensity, soil types, and water and fertility levels without, however, any variance in genotype. The color determinations are in accordance with The 2007 R.H.S. Colour Chart of The Royal Horticultural Society, London, England, except where general color terms of ordinary dictionary significance are used.

General description:

*Plant type.*—Semi-evergreen ornamental perennial grass.

*Plant habit.*—Clump-forming mound of arching leaves.

*Height and spread.*—Reaches about 11.4 cm in height, spreads to about 21.4 cm in diameter.

*Cold Hardiness.*—At least in U.S.D.A. Zone 6.

*Diseases.*—No susceptibility or resistance to diseases has been observed.

*Root description.*—Short, stout rhizomes with dense, fibrous roots, roots moderately branched.

*Propagation.*—Fan division.

*Root development from division.*—Fully develop in 9-cm containers in about 9 months from a single fan.

*Growth rate.*—Moderate.

*Branching.*—Main shoots grow from the base, no lateral branches.

*Branch quantity.*—Average of 60 shoots.

Foliage description:

*Leaf shape.*—Linear to filiform, curved.

*Leaf division*.—Simple.
*Leaf base*.—Sheathed.
*Leaf apex*.—Narrowly acute.
*Leaf aspect*.—Leaves initially emerge upright, then cascade outward and finally arch downward.
*Leaf venation*.—Parallel, color matches leaf color.
*Leaf margins*.—Entire.
*Leaf persistence*.—Persistent; evergreen under conditions tested.
*Leaf size*.—Average of 10.1 cm in length and 2.3 mm in width.
*Leaf number*.—Average of 9 leaves per shoot.
*Leaf arrangement*.—Alternate.
*Leaf surface*.—Slightly glossy and smooth on upper and lower surface.
*Leaf durability to stress*.—High.
*Leaf color*.—Young leaves upper surface; centers 143A, margins 1D, mature leaves upper surface; centers 136A with fine stripes of 136C, margins 4D, young leaves lower surface; centers N138B, margins 1D, mature leaves lower surface; centers 133B, margins 6D.
*Sheathing*.—Average of 2.5 cm in length, 2 mm in diameter, color; 157D, tinged 157A towards leaf blade.

Flower description: Flowering has not been observed to date.

It is claimed:

1. A new and distinct cultivar of *Koeleria* plant named 'Cornish Blue' as herein illustrated and described.

* * * * *